United States Patent
Watabe et al.

(10) Patent No.: US 8,831,892 B2
(45) Date of Patent: *Sep. 9, 2014

(54) CHROMATOGRAPH ANALYZING DEVICE

(75) Inventors: Osamu Watabe, Mito (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 132 days.

This patent is subject to a terminal disclaimer.

(21) Appl. No.: 13/572,442

(22) Filed: Aug. 10, 2012

(65) Prior Publication Data

US 2012/0310546 A1 Dec. 6, 2012

Related U.S. Application Data

(60) Continuation of application No. 12/633,569, filed on Dec. 8, 2009, now Pat. No. 8,249,817, which is a division of application No. 11/889,056, filed on Aug. 8, 2007, now Pat. No. 7,640,117.

(30) Foreign Application Priority Data

Aug. 31, 2006 (JP) ................................. 2006-235701

(51) Int. Cl.
G06F 19/00 (2011.01)
G01N 30/86 (2006.01)

(52) U.S. Cl.
CPC ........ *G01N 30/8675* (2013.01); *G01N 30/8631* (2013.01); *G01N 30/8651* (2013.01); *G01N 30/8641* (2013.01)
USPC .................. 702/23; 702/22; 702/30; 702/32; 73/23.36

(58) Field of Classification Search
USPC ............... 702/23, 22, 30, 32; 73/23.23, 23.36
See application file for complete search history.

(56) References Cited

U.S. PATENT DOCUMENTS

| | | | |
|---|---|---|---|
| 3,721,813 A | 3/1973 | Condon et al. | |
| 5,644,503 A * | 7/1997 | Ito et al. | ........................ 702/22 |
| 6,076,047 A * | 6/2000 | Ito et al. | ........................ 702/32 |
| 6,314,374 B1 | 11/2001 | Ito et al. | |
| 6,415,232 B1 | 7/2002 | Hayashi | |
| 6,748,333 B1 | 6/2004 | Ito et al. | |

(Continued)

FOREIGN PATENT DOCUMENTS

| | | |
|---|---|---|
| JP | 06-094696 A | 4/1994 |
| JP | 08-233795 A | 9/1996 |
| JP | 2003-161725 A | 6/2003 |

OTHER PUBLICATIONS

Office Action mailed May 22, 2012 issued in corresponding JP Patent Application No. 2006-235701.

(Continued)

*Primary Examiner* — Jonathan C Teixeira Moffat
*Assistant Examiner* — Hien Vo
(74) *Attorney, Agent, or Firm* — McDermott Will & Emery LLP

(57) ABSTRACT

A chromatograph analyzing device for automatically executing a base line setting process on an unseparated peak using preset base line conditions. The chromatograph analyzing device includes a separation unit for separating a component included in a sample, and a data processing device for identifying the component of the sample and the quantity of the component in the sample by using a chromatogram obtained from the separation.

5 Claims, 15 Drawing Sheets

(56) References Cited

U.S. PATENT DOCUMENTS

2002/0147550 A1 10/2002 Ito et al.
2004/0199336 A1 10/2004 Ito et al.
2007/0038389 A1* 2/2007 Toshima et al. ................. 702/32

OTHER PUBLICATIONS

Japanses Office Action issued in Japanse Patent Application No. 2006-235701, dated Oct. 11, 2011.

* cited by examiner

FIG. 4A
FIG. 4B
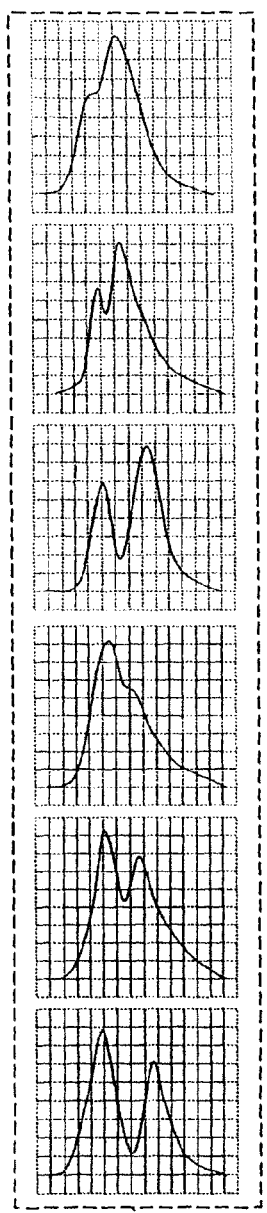
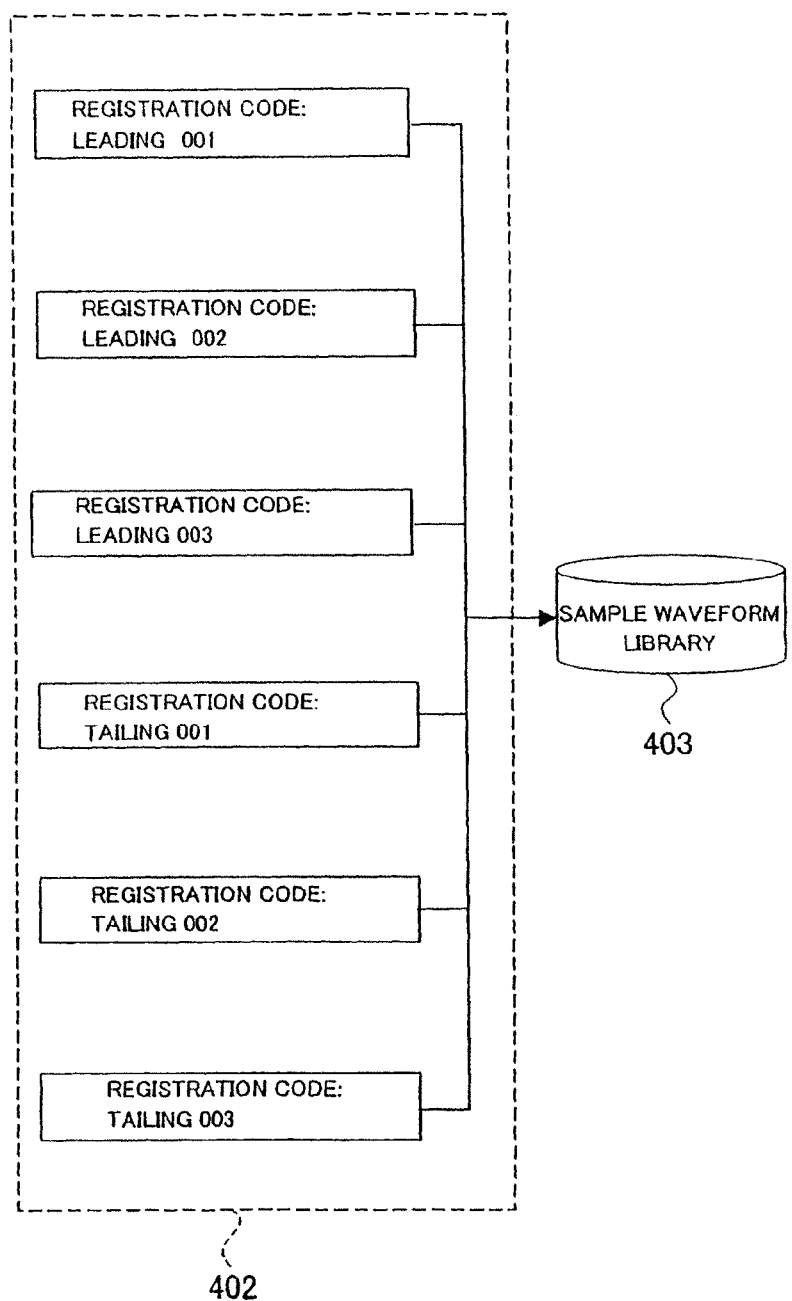
401
402

FIG. 16

| TIME | FUNCTION | NUMERICAL VALUE | On/Off |
|---|---|---|---|
| 0.0 | BASE LINE N METHOD | 0 | |
| 1.0 | FORWARD HORIZONTAL LINE | | On |
| 3.0 | FORWARD HORIZONTAL LINE | | Off |
| 3.5 | BASE LINE SETTING PROCESS | | On |
| 4.5 | BASE LINE SETTING PROCESS | | Off |
| 5.0 | BACKWARD HORIZONTAL LINE | | On |
| 5.5 | BACKWARD HORIZONTAL LINE | | Off |
| | NO WAVEFORM PROCESS | | |
| | FORWARD HORIZONTAL LINE | | |
| | MANUAL CORRECTION | | |
| | BACKWARD HORIZONTAL LINE | | |
| | . | | |
| | . | | |

~1601

NAME OF PEAK SHAPE LIBRARY | PEAK SHAPE LIBRARY 001 | ~1602

CHROMATOGRAPH ANALYZING DEVICE

CROSS-REFERENCE TO RELATED APPLICATIONS

This application is Continuation of U.S. application Ser. No. 12/633,569, filed on Dec. 8, 2009, now U.S. Pat. No. 8,249,817 which is a Divisional of U.S. application Ser. No. 11/889,056, filed on Aug. 8, 2007, (issued U.S. Pat. No. 7,640,117), claiming priority of Japanese Patent Application No. 2006-235701, filed on Aug. 31, 2006, the entire contents of each of which are hereby incorporated by reference.

BACKGROUND OF THE INVENTION

1. Field of the Invention

The present invention relates to a chromatograph analyzing device, and particularly relates to a chromatograph device having a function for processing a waveform of chromatograph data.

2. Description of the Related Art

Chromatograph data obtained by chromatograph analyzing devices are waveform data such that the abscissa axis is time and the ordinate axis is signal intensity. A relationship between the time and a component is given in advance. Therefore, a position of a peak of mountain wave portion of the waveform data on the abscissa axis represents a type or name of the component. On the other hand, an area of a mountain wave portion of the waveform data represents an amount of contained material in the component. A process for identifying the component based on the peak position of mountain wave portion is called a qualitative process. A process for calculating the area of the mountain wave portion so as to identify the amount of contained material in the component is called a quantitative calculation process.

A so-called unseparated peak occasionally appears among mountain wave portions of the waveform data. The unseparated peak appears as one mountain wave portion when two mountain wave portions are slightly shifted from each other. In order to identify a component based on the unseparated peak so as to calculate the amount of the contained material in the component, it is necessary to identify two mountain wave portions included in the unseparated peak.

The quantitative calculation process is executed by a waveform process using a computer. In the quantitative calculation process, it is necessary for determining an area of a mountain wave portion to set a base line. In general, it is difficult to set an accurate base line with respect to an unseparated peak.

A user occasionally cannot satisfy a base line with respect to an unseparated peak set by a computer. In this case, the user manually corrects the base line set by the computer. This is called a manual base line correcting process.

In the manual base line correcting process, a user manually sets a base line with respect to an unseparated peak. The setting of a base line depends on user's experience and knowledge. Therefore, the results of the quantitative calculation process for the unseparated peak subject to the manual base line correcting process have greatly dispersed accuracy.

Chromatograph data is occasionally collected online. In this case, the quantitative calculation process is executed at real time. It is, however, difficult to execute the manual base line correcting process at real time.

SUMMARY OF THE INVENTION

It is an object of the present invention to provide a chromatograph analyzing device in which results of a quantitative calculation process for unseparated peaks have less dispersion or the results are more accurate.

The present invention relates to a chromatograph device having a waveform processing function. According to the chromatograph analyzing device of the present invention, a base line setting process is automatically executed on an unseparated peak by using base line setting conditions set in advance.

According to the chromatograph analyzing device of the present invention, results of a quantitative calculation process on the unseparated peak have less dispersion or are more accurate.

BRIEF DESCRIPTION OF THE DRAWINGS

FIGS. 4A and 4B illustrate a data structure of sample waveforms of unseparated peak waveform registered in the chromatograph analyzing device according to the present invention;

FIG. 16 is a diagram illustrating an example of a time table information setting screen for the waveform process displayed on the display device of the chromatograph analyzing device according to the present invention.

DESCRIPTION OF THE PREFERRED EMBODIMENT

Figure 1:
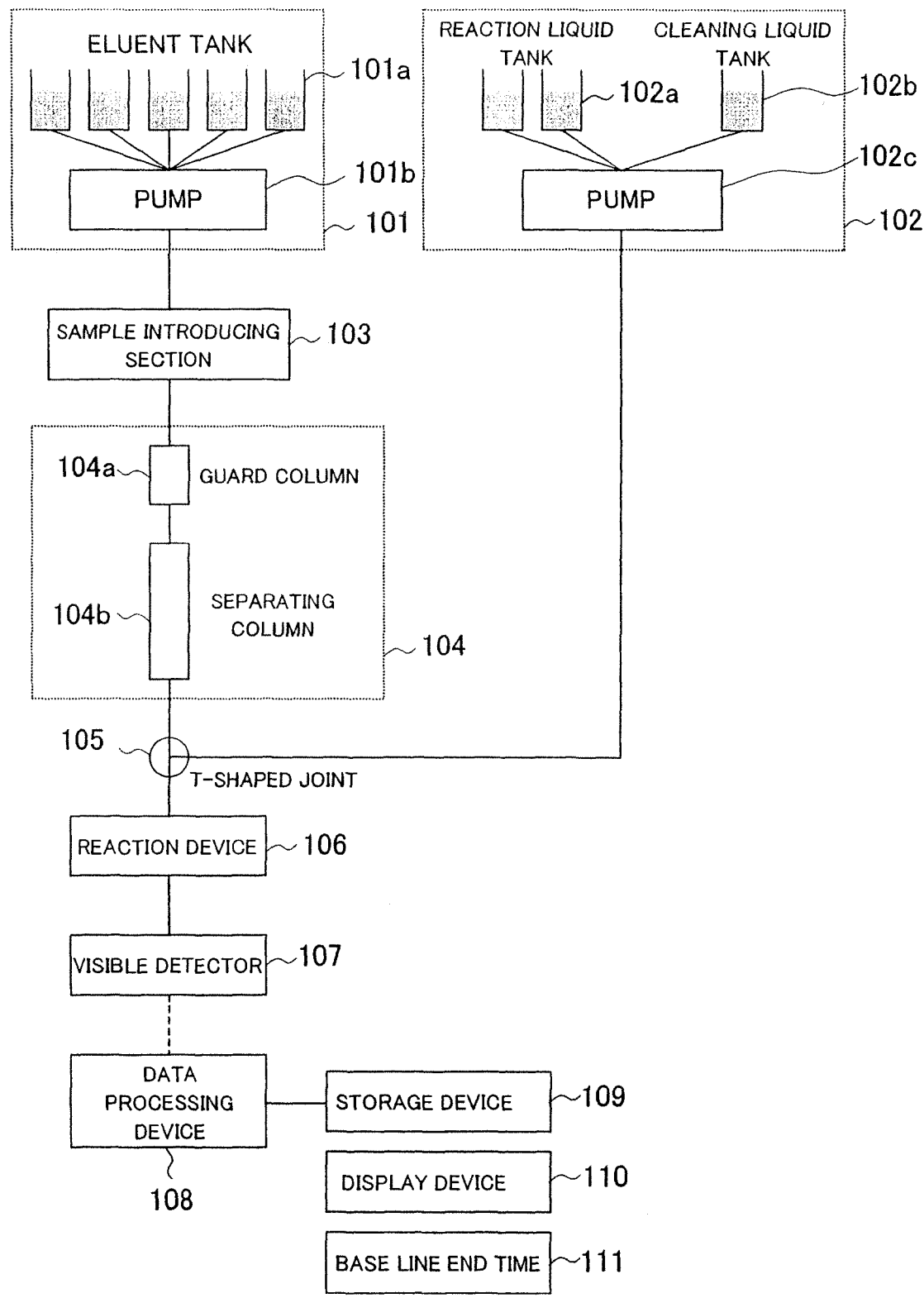
FIG. 1 is a diagram illustrating a configuration of a chromatograph analyzing device according to the present invention.

FIG. 1 illustrates a configuration example of a chromatograph analyzing device of the present invention. The chromatograph analyzing device of this example includes an eluent sending mechanism 101, a reaction liquid sending mechanism 102, a sample introducing section 103, a separating mechanism 104, a T-shaped joint 105, a reaction device 106, and a visible detector 107. They are connected by a flow passage. The chromatograph analyzing device further includes a data processing device 108, a storage device 109, a display device 110 and an input device 111. The data processing device 108 may include a computer. The storage device 109 is provided with a peak shape library and a sample waveform library.

The eluent sending mechanism 101 has a plurality of eluent tanks 101a and a pump 101b, and a solenoid valve which connects one of the eluent tanks 101a to the pump 101b is provided. The solenoid valve may be provided in the pump 101b, but may be provided between the eluent tanks 101a and the pump 101b. The solenoid valve is switched by a signal from the data processing device 108 or direct input into the pump 101b.

The reaction liquid sending mechanism 102 includes a plurality of reaction liquid tanks 102a, a cleaning liquid tank 102b and a pump 102c. A solenoid valve which connects one of both the reaction liquid tanks 102a and the cleaning liquid tank 102b to the pump 102c is provided. The solenoid valve may be provided into the pump 102c but may be provided between the pump 102c and both the reaction liquid tanks 102a and the cleaning liquid tank 102b. The solenoid valve is switched by a signal from the data processing device 108 or direct input into the pump 102c.

The separating mechanism 104 has a plurality of guard columns 104a and a separating column 104b. A column switching valve is provided so as to connect one of the guard columns 104a to the separating column 104b.

The eluent from the eluent tank 101a is sent to the sample introducing section 103 by the pump 101b. A sample liquid and the eluent are sent from the sample introducing section 103 to the separating mechanism 104. The sample liquid and the eluent pass through the guard column 104a and a predetermined sample is separated in the separating column 104b so as to be sent to the T-shaped joint 105.

The reaction liquid from the reaction liquid tank 102a is sent to the T-shaped joint 105 by the pump 102c. The sample and the reaction liquid are mixed in the T-shaped joint 105, so that a mixed liquid is prepared. The mixed liquid is sent to the reaction device 106. In the reaction device 106, the sample reacts to the reaction liquid and takes on a color. The colored sample is detected by the visible detector 107. A detected signal from the visible detector 107 is sent to the data processing device 108. The data processing device 108 processes an input signal so as to create chromatogram and data. The chromatogram and data are saved in the storage device 109 and are displayed on the display device 110.

A basic flow of the analyzing processing in a conventional chromatograph analyzing device is described with reference to FIG. 2. A user checks connection of each unit composing the chromatograph analyzing device at step S201, and when no problem arises, each unit is warmed up so that the analyzing process can be started. The user creates analyzing conditions to be used for the analyzing process via the input device 111 at step S202. The analyzing conditions include setting parameters of each unit, qualitative process conditions, quantitative calculation process conditions and waveform processing conditions. The qualitative process conditions relate to a method of identifying a component of a sample. For example, a range for identifying each component on an abscissa axis is set. The quantitative calculation process conditions relate to a method of calculating an amount of a contained material. That is to say, they are conditions of a method for calculating an area of a mountain wave portion of waveform data. The waveform processing conditions are conditions of a waveform process necessary for the quantitative calculation process.

The user creates sample conditions via the input device 111 at step S203. The sample conditions include information about the sample and analyzing cycle conditions. For example, the sample conditions include, for example, the number of standard samples, the number of samples to be measured, and the introducing order of the standard samples and the samples to be measured.

The standard samples and the samples to be measured are measured by the chromatograph analyzing device at step S204. The samples to be measured are specified in a sample table in advance. The data processing device 108 analyzes measured data at step S205. The analyzed results as well as the analyzing conditions are recorded and saved in the storage device 109.

A determination is made at step S206 whether the analyzed results of all the samples to be measured specified on the sample table are obtained. When the analyzed result of all the samples are not obtained, the sequence returns to step S204 so that the samples are measured. When the analyzed results of all the samples are obtained, the sequence goes to step S207.

At step S207, the user examines the analyzed results displayed on the display device 110, and a determination is made whether the reanalysis is necessary. When the determination is made that the reanalysis is not necessary, the sequence goes to step S211. When the reanalysis is necessary, the sequence goes to step S208.

The reanalysis is conducted at step S208. The user executes the manual base line correcting process with respect to an unseparated peak.

The analyzed results are examined and a determination is made whether the reanalysis is further necessary at step S209. When the determination is made that the reanalysis is necessary, the sequence returns to step S208. When the reanalysis is not necessary, the reanalyzed results as well as the base line setting conditions are recorded and saved in the storage device 109 at step S210. A determination is made whether another analyzing process is necessary at step S211. When another analyzing process is necessary, the sequence goes to step S202, so that the analyzing process is again executed. When another analyzing process is not necessary, this process is ended.

Figure 3:
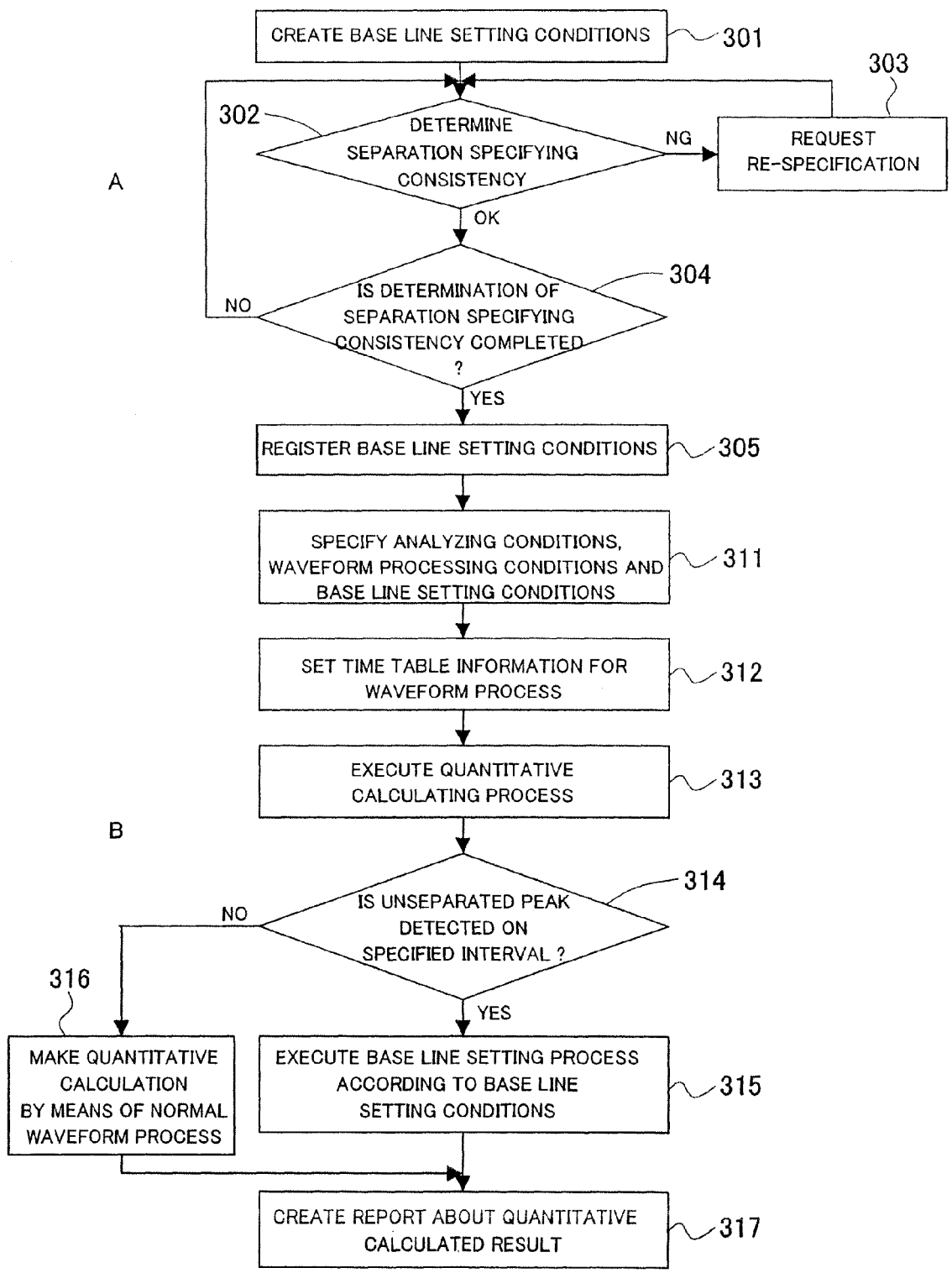
FIG. 3 is a flowchart diagram explaining user's operations for automatically executing a base line setting process in the analyzing process using the chromatograph analyzing device according to the present invention.

In reference to FIG. 3, steps 301 to 313 are referred to as part A and steps 314-317 are referred to as part B, as shown in FIG. 3. A process for registering the baseline setting conditions to be used for the base line setting process in the chromatograph analyzing device of the present invention is described with reference to FIG. 3, part A. The user creates the base line setting conditions via the input device 111 at step S301. The baseline setting conditions include a sample waveform and an unseparated peak separating method. The sample waveform is a template of the unseparated peak expected to appear in the chromatograph data. The unseparated peak separating method is a method for separating two waveforms from a sample waveform.

The data processing device of the chromatograph analyzing device of the present invention checks the base line setting condition for separation specifying consistency determination at step S302. In the check process of the separation specifying consistency determination, a calculation is made by using the base line setting conditions, and a determination is made whether its result diverges or converges. When the result diverges, the determination is made as inconsistent, and when the result converges, the determination is made as consistent.

When the baseline setting conditions are inconsistent, the result of the check process for the separation specifying consistency determination is determined as an error. In this case, re-specification of the base line setting conditions is requested at step S303.

When the base line setting conditions are consistent, the result of the check process for the separation specifying consistency determination is determined as normal. At step 304, a determination is made whether the check of the separation specifying consistency determination with respect to the base line setting conditions is completed. When the check is not completed, the sequence returns to step S302. When the check is completed, the base line setting condition is saved in the storage device and is registered in the peak shape library at step S305.

In this embodiment, the base line setting process is executed by using the base line setting conditions registered in the peak shape library. Therefore, the base line setting process can be executed automatically at real time.

A basic flow of the analyzing process in the chromatograph analyzing device of the present invention is described with reference to FIG. 3, part B. The user specifies the analyzing conditions, the waveform processing conditions and the base line setting conditions in the peak shape library at step S311. The user creates a time table for waveform processing on a time table information setting screen for waveform processing at step S312. Namely, the user specifies a waveform processing interval to be subject to the base line setting process. An example of the time table information setting screen for waveform processing is described with reference to FIG. 16.

The data processing device of the chromatograph analyzing device of the present invention executes a quantitative calculation process based on the analyzing conditions and the waveform processing conditions specified at step S311 according to the waveform process time table created at step S312.

The data processing device determines whether an unseparated peak is detected in the specified waveform processing interval at step S314. When the unseparated peak is detected, the sequence goes to step S315. When the unseparated peak is not detected, the sequence goes to step S316.

The data processing device executes the base line setting process according to the base line setting conditions at step S315. The data processing device compares the detected unseparated peak with the sample waveforms, and selects a plurality of sample waveforms which are determined to be approximate to the unseparated peak or a sample waveform which is determined to be the most approximate to the unseparated peak. The data processing device separates each of the sample waveforms into two peaks using the specified separating method. Areas of the two mountain wave portions of each sample waveform are calculated.

The data processing device executes the quantitative calculation process according to a normal waveform process at step S316. Finally, the result of the quantitative calculation process is recorded and saved at step S317.

Figure 2:
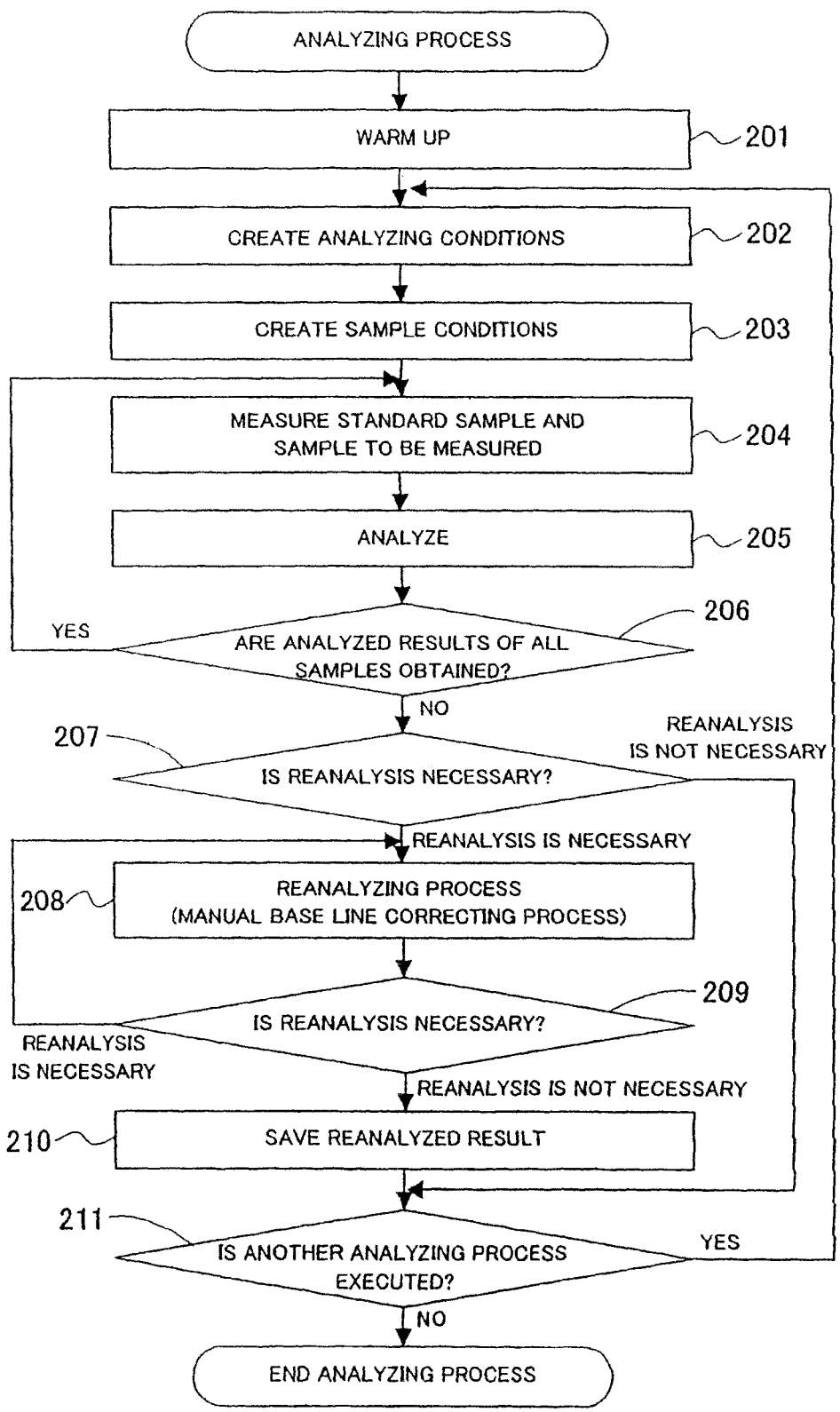
FIG. 2 is a diagram illustrating a flow of a basic analyzing process using a conventional chromatograph analyzing device.

In the conventional chromatograph analyzing device in FIG. 2, the data processing device 108 conducts the analysis at step S205, and the user executes the manual base line correcting process at step S208. In the chromatograph analyzing device of the present invention, however, the data processing device 108 executes the base line setting process at step S315, and thus the manual base line correcting process by the user is not necessary. In the chromatograph analyzing device of the present invention, therefore, even when the chromatograph data is supplied online, the quantitative calculation process can be executed on the chromatograph data at real time. In the chromatograph analyzing device of the present invention, the base line setting process is executed on the unseparated peak according to the base line setting conditions specified by the user. For this reason, the result of the quantitative calculation process can reflect a user's preference.

Examples of the sample waveforms provided by the chromatograph analyzing device of the present invention are described with reference to FIGS. 4A and 4B. The sample waveforms 401 include a plurality of curve profiles having typical leading shape and tailing shape. The sample waveforms 401 are provided with registration codes 402, respectively, and are saved in a sample waveform library 403. The sample waveforms provided as standard ones and the sample waveforms manually created and registered by the user are saved in the sample waveform library 403.

A method that the user manually creates the sample waveforms is explained with reference to FIGS. 5 and 6. The user may correct the sample waveforms saved in the sample waveform library 403, but may draw sample waveforms by oneself.

Figure 5:
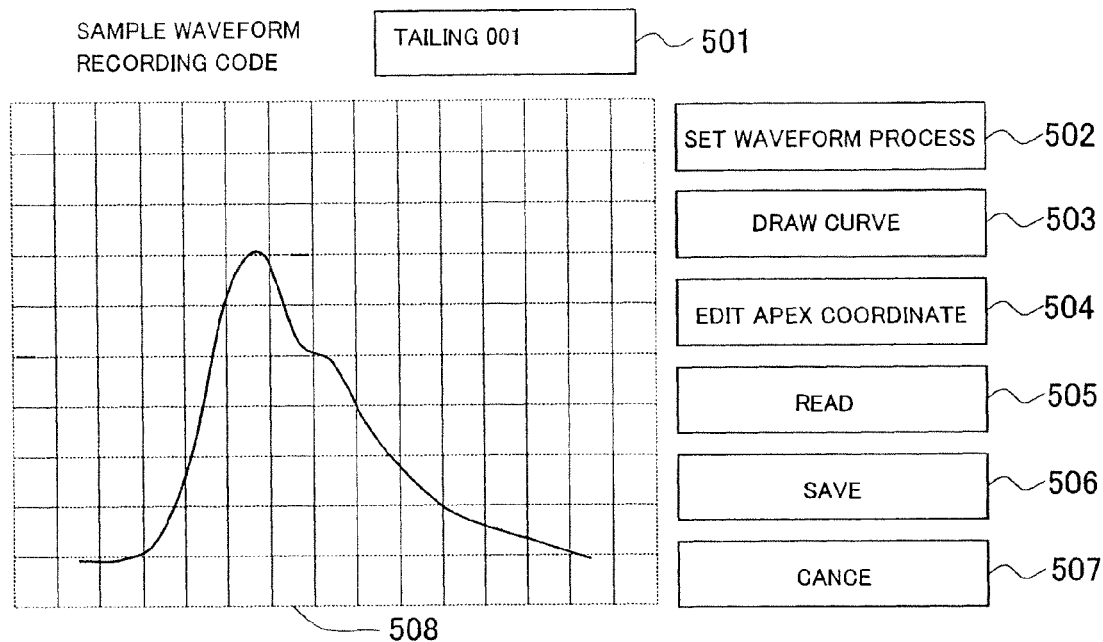
FIG. 5 is a diagram illustrating an example of a sample waveform editing screen displayed on a display device of the chromatograph analyzing device according to the present invention.

FIG. 5 illustrates an example of a sample waveform editing screen displayed on the display device. This editing screen includes a sample waveform registration code field 501, a waveform process setting button 502, a curve drawing button 503, an apex coordinate edit button 504, a read button 505, a save button 506, a cancel button 507 and a graph region 508. A on-creating or created sample waveform is displayed on the graph region 508.

The user inputs a code of a sample waveform to be created into the sample waveform registration code field 501. When the user clicks the waveform process setting button 502, the waveform process setting screen in FIG. 7 is displayed. When the user clicks the curve drawing button 503, a sample waveform which expresses a desired unseparated peak waveform can be drawn on the graph region 508. When the user clicks the apex coordinate edit button 504, a screen shown in FIG. 6 is displayed, apexes of the sample waveform curve displayed on the graph region 508 is displayed. When the user clicks the read button 505, the sample waveform saved in the sample waveform library 403 is read so as to be capable of being displayed on the graph region 508. When the user clicks the save button 506, the sample waveform displayed on the graph region 508 is provided with the sample waveform registration code 501, to be saved in the sample waveform library 403. When the user clicks the cancel button 507, the previous process can be restored.

When the sample waveform creating process is ended or the sample waveform creating process is not executed, the user clicks the waveform process setting button 502. As a result, a waveform process setting screen in FIG. 7 is displayed.

Figure 6:
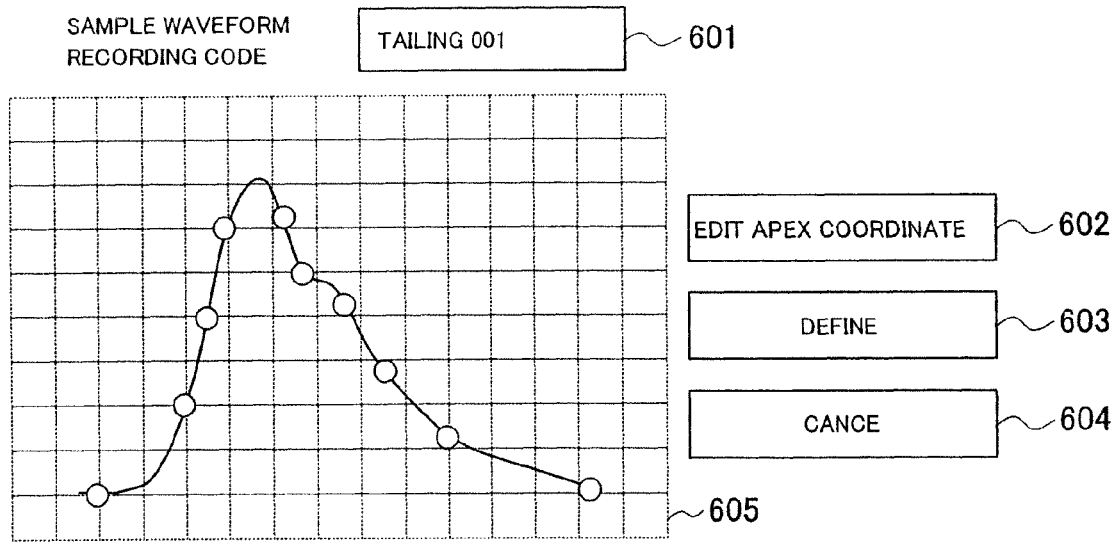
FIG. 6 is a diagram illustrating an example of a sample waveform apex display screen displayed on the display device of the chromatograph analyzing device according to the present invention.
Figure 7:
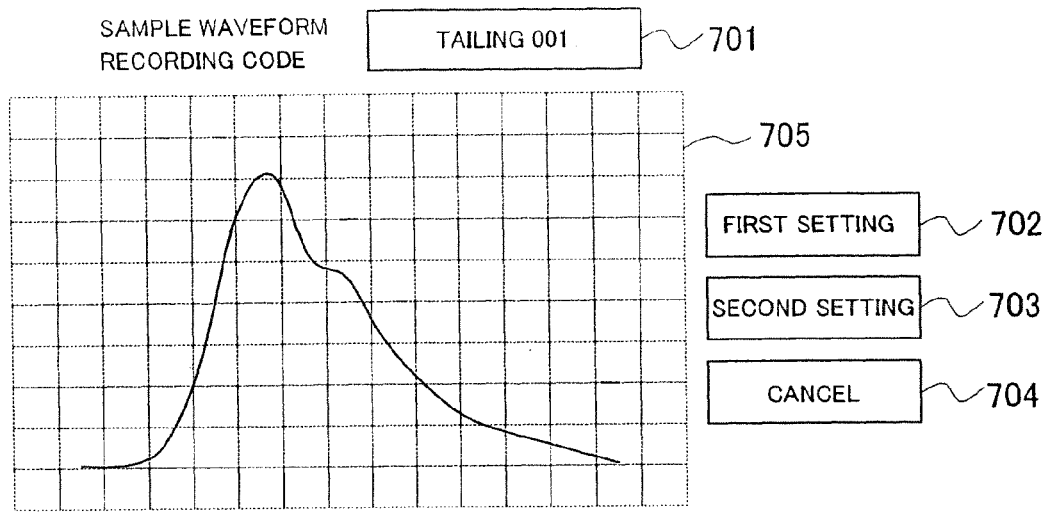
FIG. 7 is a diagram illustrating an example of a separating method setting process screen displayed on the display device of the chromatograph analyzing device according to the present invention.

FIG. 6 illustrates an example of a sample waveform apex display screen displayed on the display device. When the user clicks the apex coordinate edit button 504 on the sample waveform editing screen of FIG. 5, the sample waveform apex display screen of this example is displayed. The sample waveform apex display screen includes a sample waveform registration code field 601, an apex coordinate edit button 602, a define button 603, a cancel button 604, and a graph region 605. A sample waveform curve with apexes (circular marks) is displayed on the graph region 605. The apexes are given onto the curve by computer software. When the user clicks the apex coordinate edit button 602, the user can edit the apexes of the curve displayed on the graph region 605. For example, the user drags the circular mark representing the apex so as to move the apex.

When a curve without an apex is displayed on the graph region 605, the apex coordinate edit button 602 is clicked so that apexes can be given to the curve displayed on the graph region 605. When the correction of the apex position is ended, the define button 603 is clicked. As a result, the display returns to the sample waveform editing screen shown in FIG. 5.

A method of setting the base line setting conditions to be used for the base line setting process is described with reference to FIGS. 7 to 15. The base line setting conditions includes a method of separating the sample waveform from the unseparated peak. The sample waveform is a template of an unseparated peak expected to appear on the chromatograph data. The unseparated peak separating method is a method for separating two peak waveforms from the sample waveform. Two setting methods are described below. The first setting method uses an existing automatic separating method. The existing automatic separating method includes EMG (Exponentially Modified Gaussian) model fitting, spline function approximation and normal distribution approximation. The second setting method uses a separating method specified by a user and a base line specified by the user. The separating method specified by the user includes a vertical line method, a forward horizontal line method, and a backward horizontal line method.

Figure 8:
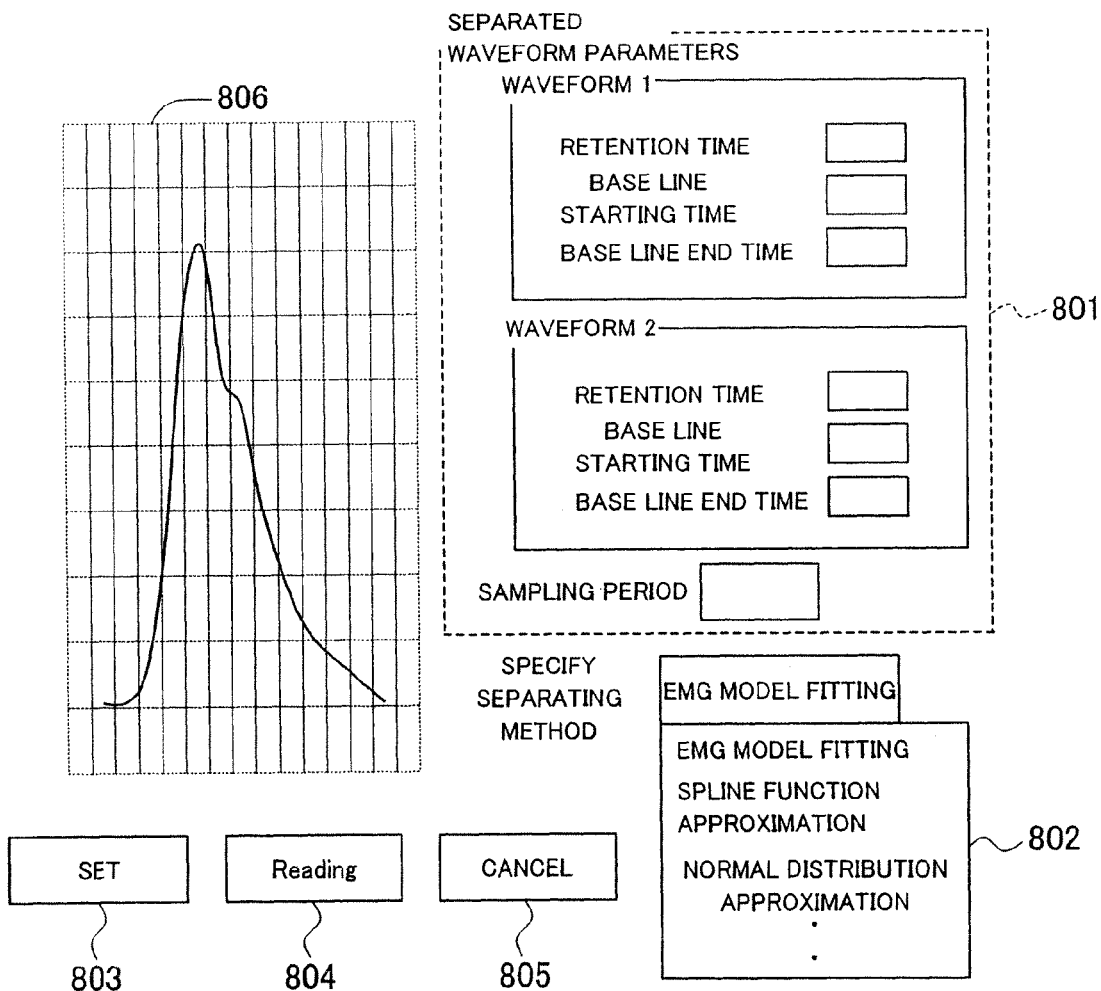
FIG. 8 is a diagram illustrating an example of a first setting process screen displayed on the display device of the chromatograph analyzing device according to the present invention.
Figure 12:
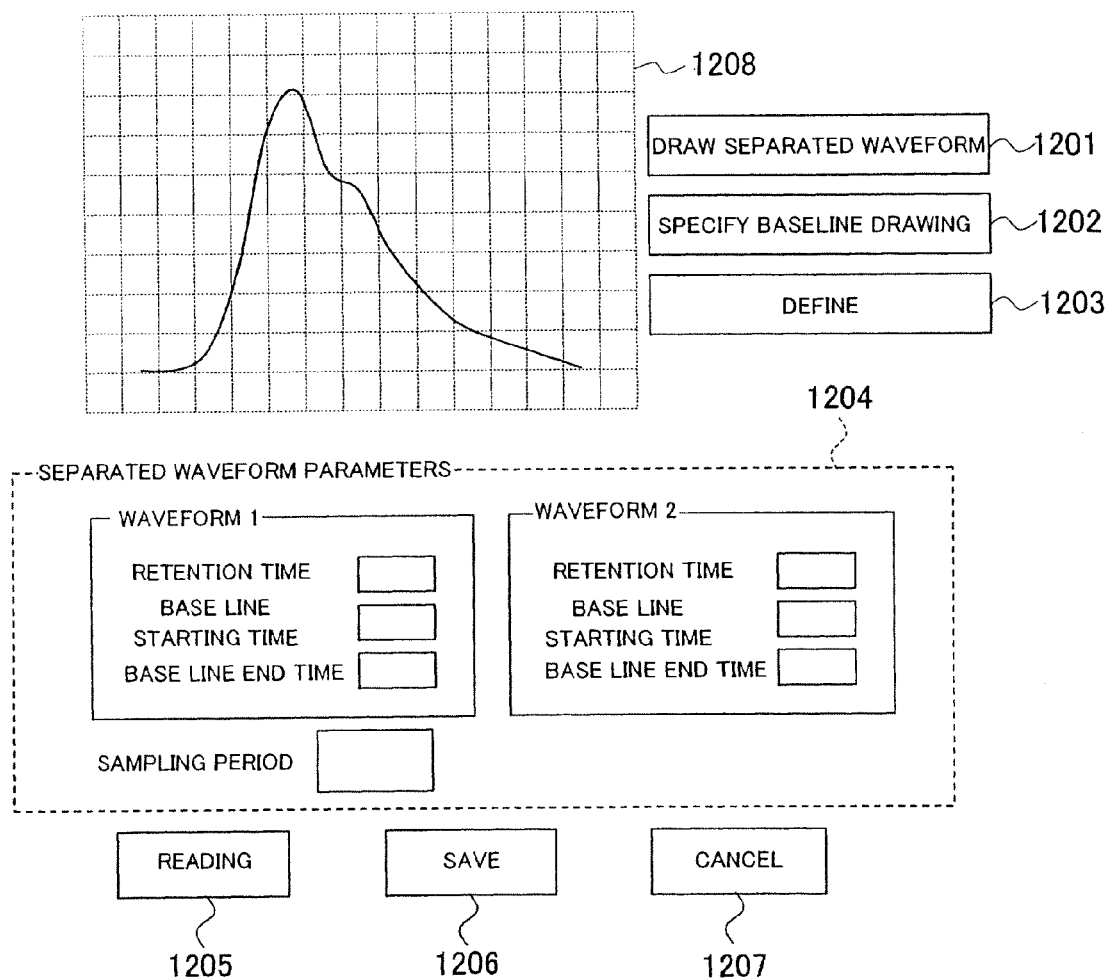
FIG. 12 is a diagram illustrating an example of a second setting process screen displayed on the display device of the chromatograph analyzing device according to the present invention.

FIG. 7 illustrates an example of the waveform process setting screen displayed on the display device. When the user clicks the waveform process setting button 502 in FIG. 5, the waveform process setting screen of this example is displayed. The waveform setting process screen includes a sample waveform registration code field 701, a first setting button 702, a second setting button 703, a cancel button 704, and a graph region 705. A sample waveform to be subject to the waveform process is displayed on the graph region 705. When the user clicks the first setting button 702, the first setting process screen shown in FIG. 8 is displayed. When the user clicks the second setting button 703, the second setting process screen shown in FIG. 12 is displayed.

FIG. 8 illustrates an example of the first setting process screen displayed on the display device. When the user clicks the first setting button 702 on the waveform process setting screen in FIG. 7, a first setting process screen of this example is displayed. The first setting process screen of this example has a separated waveform parameter setting field 801, a separating method specifying field 802, a setting button 803, a read button 804, a cancel button 805 and a graph region 806. A sample waveform to be subject to the first setting process is displayed on the graph region 806.

Parameters of separated waveforms to be used commonly for the first setting process are displayed on the separated waveform parameter setting field 801. The parameters include retention time showing the time of an apex of a separated waveform, base line starting time, base line end time and sampling period. The user sets desired values as the parameters of the separated waveform, so as to be capable of setting two waveform shapes included in the unseparated peak waveform. The separating method for the sample waveform is displayed on the separating method specifying field 802. The user can select a desired separating method as the separating method for separating two wavefonus from the unseparated peak. The separating method includes EMG model fitting, spline function approximation, and normal distribution approximation. These separating methods are well known, and thus they are not described here. For example, as to details of the EMG model fitting, refer to Japanese Patent Application Laid-Open No. 2003-161725.

The user sets desired parameters on the separated waveform parameter setting field 801, specifies a desired separating method on the separating method specifying field 802, and clicks the setting button 803. The case where the EMG model fitting is specified as the separating method is described here. When the user clicks the setting button 803, a screen where parameters of the EMG model fitting in FIG. 9 is set is displayed.

When the user clicks the read button 804, the separated waveform parameters and the separating method set by the first setting process as well as the sample waveform can be read. When the user clicks the cancel button 805, the previous process can be canceled.

Figure 9:
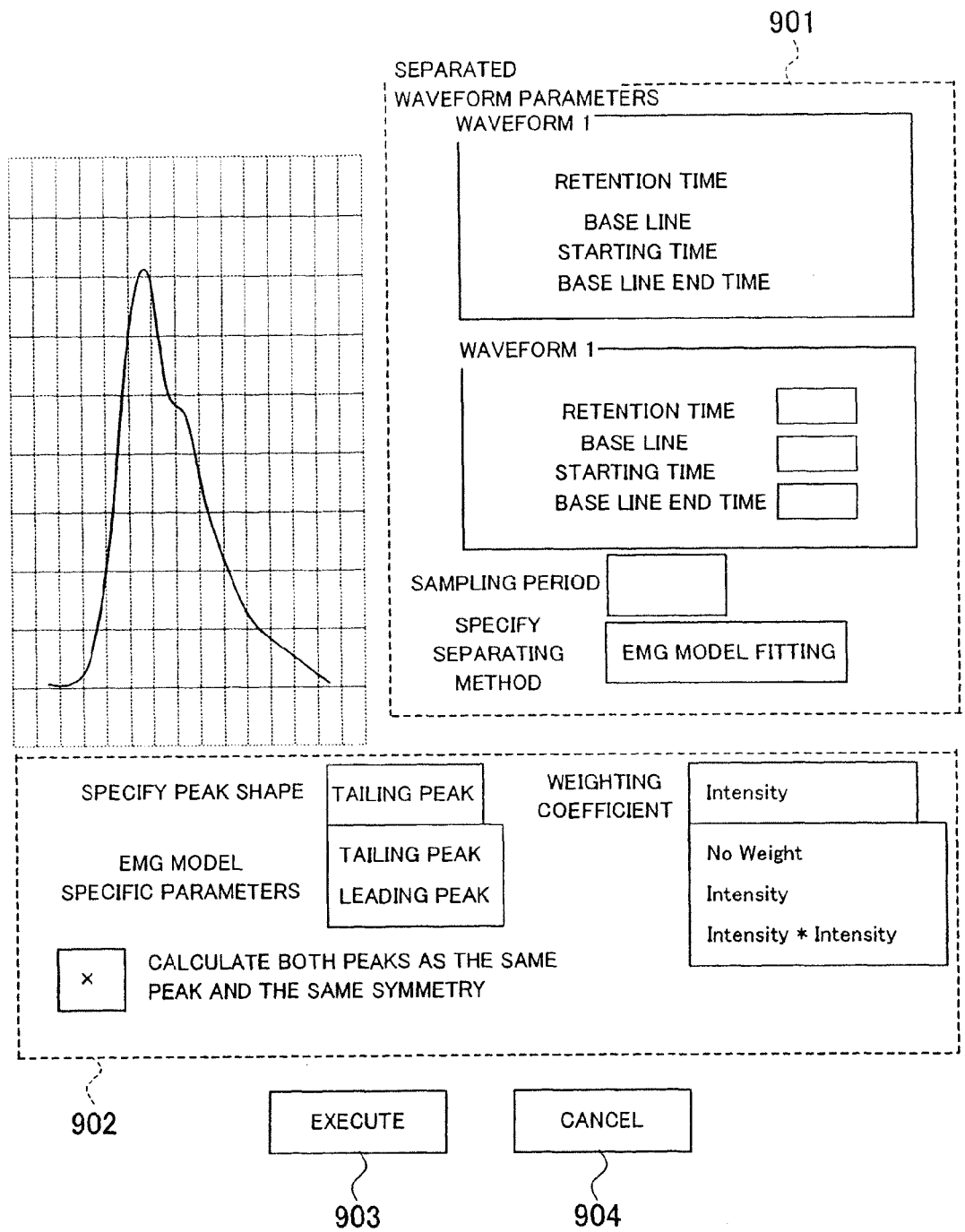
FIG. 9 is a diagram illustrating an EMG (Exponentially Modified Gaussian) model fitting parameter setting screen displayed on the display device of the chromatograph analyzing device according to the present invention.

FIG. 9 illustrates an example of the EMG model fitting parameter setting screen displayed on the display device. The EMG model fitting is specified on the separating method specifying field 802 of the first setting process screen in FIG. 8, and the setting button 803 is clicked. As a result, the EMG model fitting parameter setting screen of this example is displayed. The EMG model fitting parameter setting screen of this example has a separated waveform parameter setting field 901, a specific parameter setting field 902, an execute button 903 and a cancel button 904.

The separated waveform parameters and the separating method used commonly for the first setting process are displayed on the separated waveform parameter setting field 901. The parameters set on the separated waveform parameter setting field 801 of the first setting process screen in FIG. 8 and the separating method specified on the separating method specifying field 802 are displayed. The user can check the separated waveform parameters and the separating method to be used commonly for the first setting process on the separated wavefoim parameter setting field 901.

The user sets specific parameters for the separating process using the EMG model fitting on the specific parameter setting field 902. The parameters include peak shape specification and weighting coefficient. The user sets the parameters in the specific parameter setting field 902 and clicks the execute button 903 so that the separating process is executed.

Figure 10:
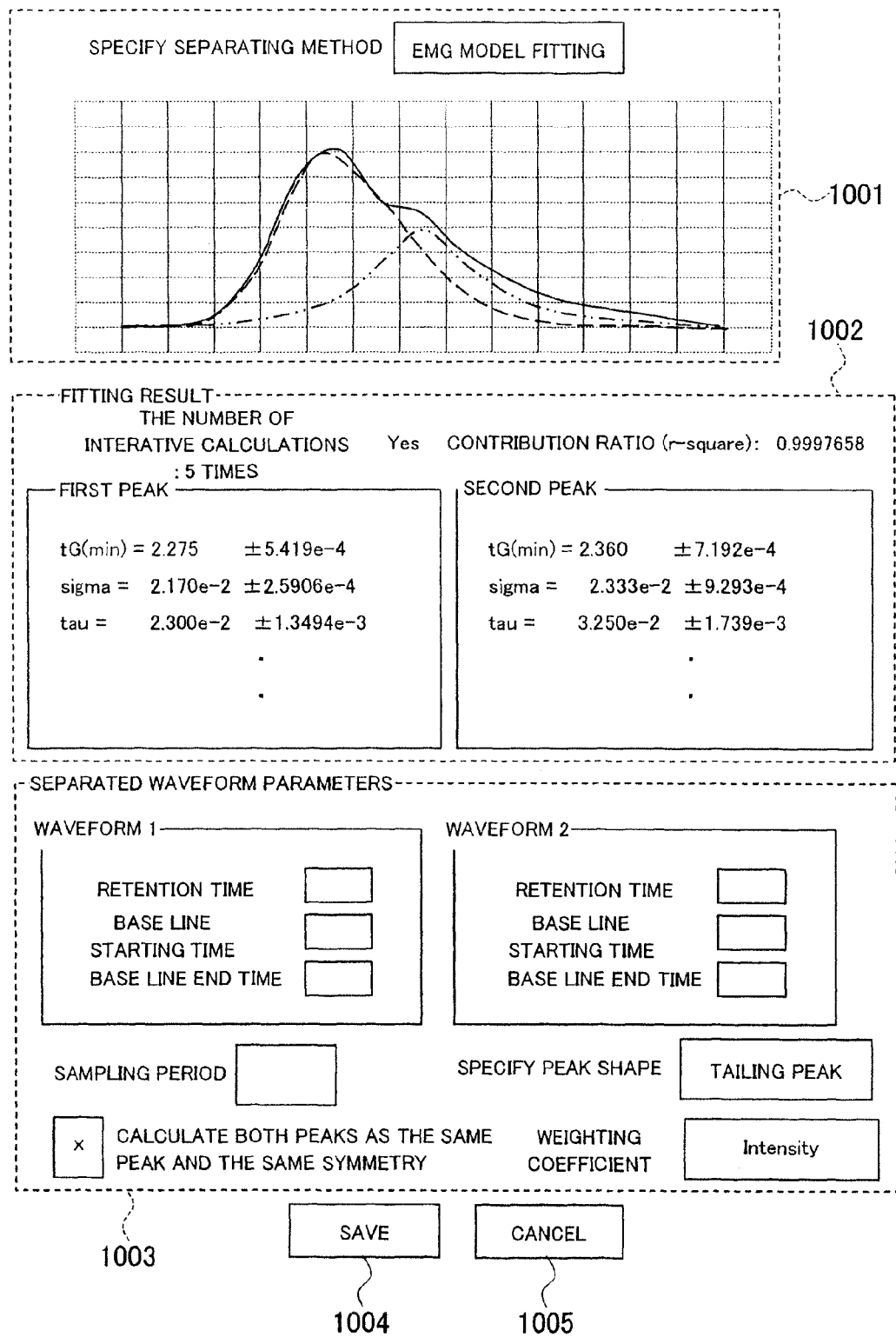
FIG. 10 is a diagram illustrating an example of a separating process result display screen displayed on the display device of the chromatograph analyzing device according to the present invention.

FIG. 10 illustrates an example of a separating process result display screen displayed on the display device. The separating process is executed by using the EMG model fitting. When the user clicks the execute button 903 on an EMG model fitting parameter setting screen separating process result display screen of FIG. 9, the separating process result display screen of this example is displayed. The separating process result display screen of this example has a graph region 1001, a fitting result display field 1002, a separating waveform parameter display field 1003, a save button 1004 and a cancel button 1005. The separating method specified on the separating method specifying field 802 of the first setting process screen in FIG. 8 is displayed on an upper end of the graph region 1001. Two waveforms separated from the sample waveform are displayed on the center of the graph region 1001. The number of iterative calculations and constants of the separated two peaks are displayed on the fitting result display field 1002. The parameters set on the separated waveform parameter setting field 801 of the first setting process screen in FIG. 8 and on the specific parameter setting field 902 of the EMG model fitting parameter setting screen in FIG. 9 are displayed on the separated waveform parameter display field 1003. When the user clicks the save button 1004, the separating method and the separating process result displayed on this screen are saved in the peak shape library.

Figure 11:
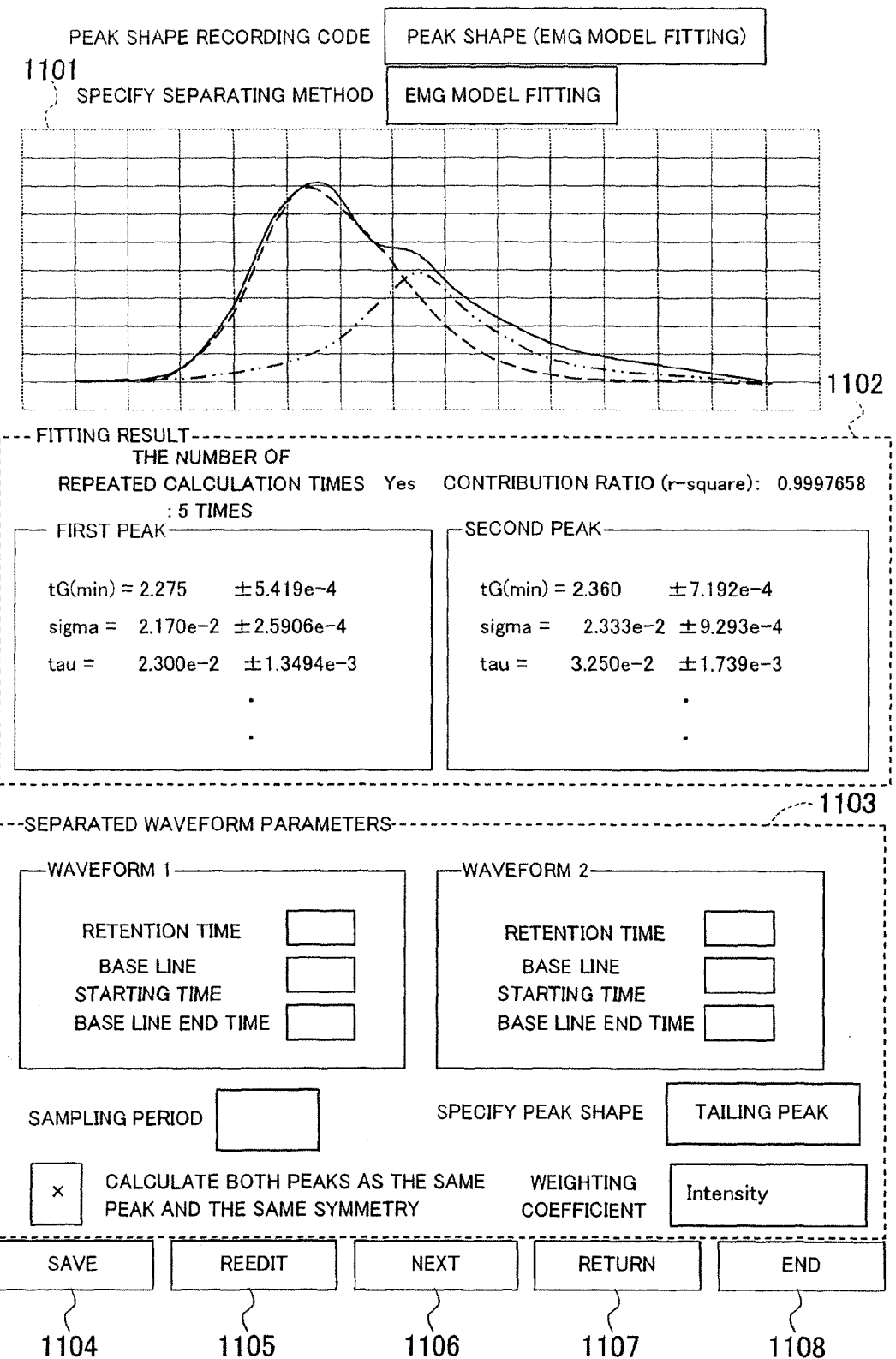
FIG. 11 is a diagram illustrating a separating process result display screen by means of a viewer function displayed on the display device of the chromatograph analyzing device according to the present invention.

FIG. 11 illustrates an example of the separating process result display screen displayed on the display device. The example of the separating process result saved in the peak shape library can be displayed by using a viewer function. The separating process result display screen of this example has a graph region 1101, a fitting result display field 1102, a separated waveform parameter display field 1103, a save button 1104, a reedit button 1105, a next button 1106, a return button 1107 and an end button 1108.

A different point from the separating process result display screen of FIG. 10 is described below. A peak shape registration code as the registration code of the peak shape library is displayed on an upper end of the graph region 1101.

When the user clicks the reedit button 1105, the separating method created by the first setting process can be reedited. When the user clicks the save button 1104, the reedited result can be saved in the peak shape library. When the user clicks the next button 1106, a next separating method saved in the peak shape library is displayed. When the user clicks the return button 1107, a previous separating method saved in the peak shape library is displayed. When the user clicks the end button 1108, the display on the separating process result display screen can be ended.

FIG. 12 illustrates an example of a second setting process screen displayed on the display device. When the user clicks the second setting button 703 on the waveform process setting screen in FIG. 7, the second setting process screen of this example is displayed. The second setting process screen of this example has a separated waveform drawing button 1201, a base line drawing button 1202, a define button 1203, a separated waveform parameter field 1204, a read button 1205, a save button 1206, a cancel button 1207 and a graph region 1208. A sample waveform for which a separating method will be set is displayed on the graph region 1208.

Separated waveform parameters to be used commonly for the second setting process are displayed on the separated waveform parameter setting field 1204. The parameters include retention time showing time of an apex of the separated waveform, base line starting time, base line end time and sampling period. The user sets desired values as the separated waveform parameters so as to be capable of separating the unseparated peak waveform into two waveforms.

Figure 13:
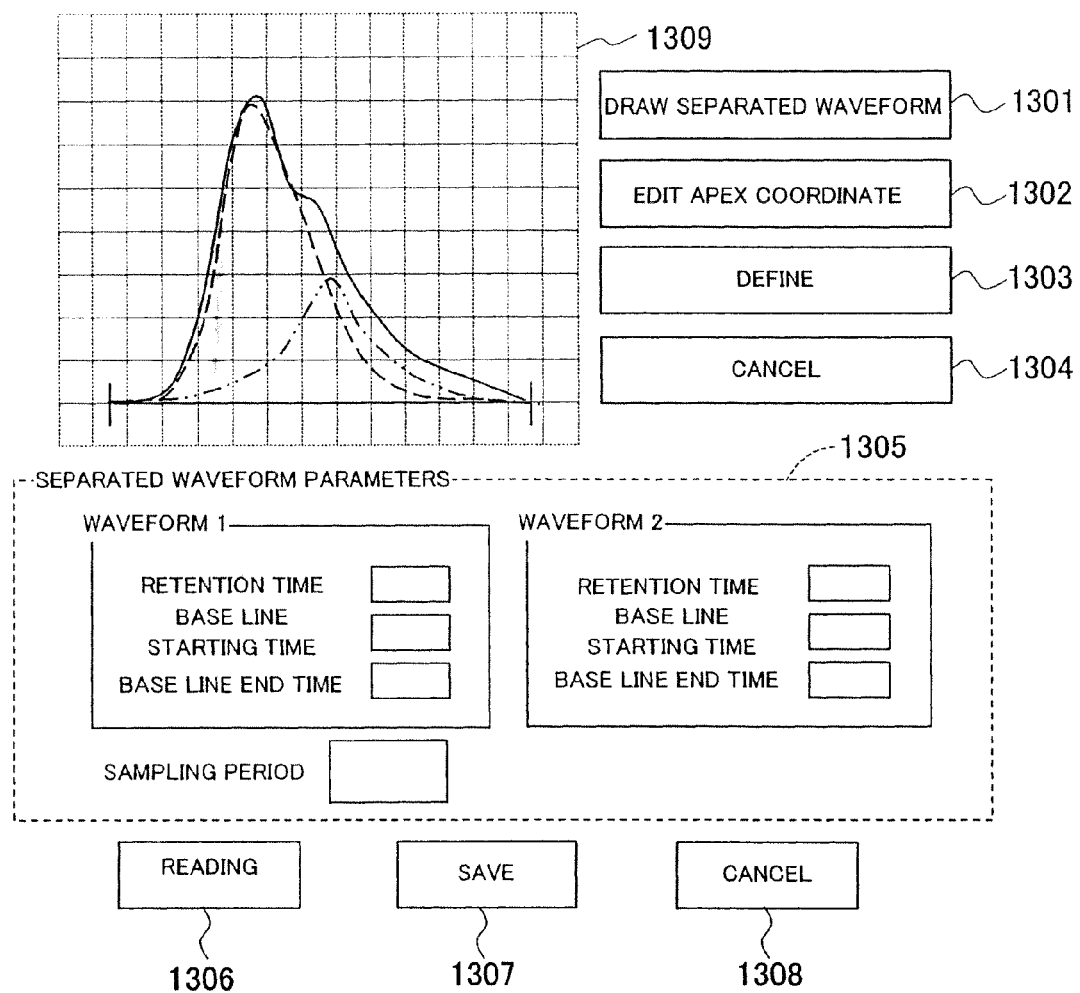
FIG. 13 is a diagram illustrating an example of a separated waveform drawing screen displayed on the display device of the chromatograph analyzing device according to the present invention.
Figure 14:
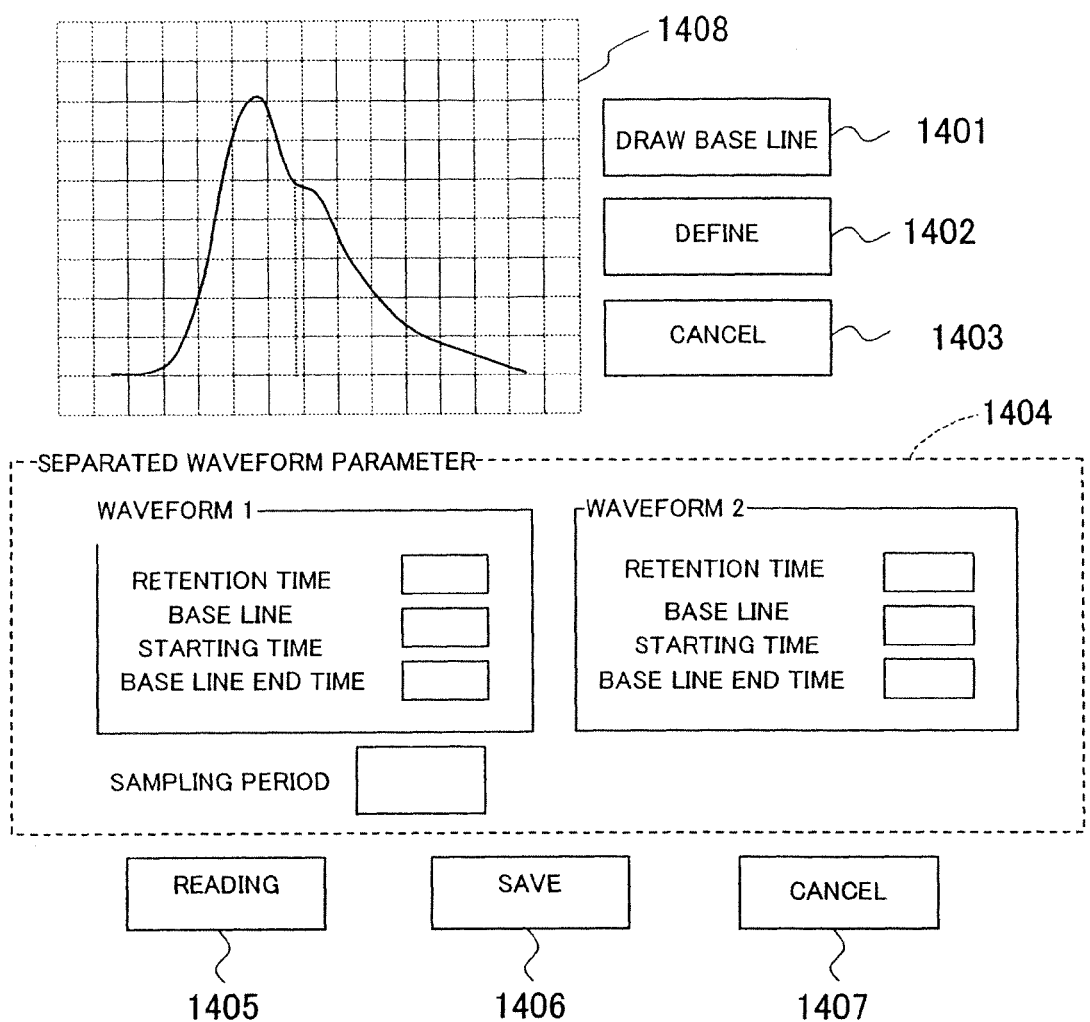
FIG. 14 is a diagram illustrating an example of a base line drawing screen displayed on the display device of the chromatograph analyzing device according to the present invention.

The user sets predetermined separated waveform parameters on the separated waveform parameter setting field 1204, and clicks the separated waveform drawing button 1201. As a result, a separated waveform drawing screen in FIG. 13 is displayed. When the user clicks a base line drawing button 1202, a base line drawing screen in FIG. 14 is displayed.

When the user clicks the read button 1205, the separating method created by the second setting process can be read. When the user clicks the save button 1206, information on the screen is saved. When the user clicks the cancel button 1207, the previous process can be cancelled.

FIG. 13 illustrates an example of a separated waveform drawing screen displayed on the display device. When the user clicks the separated waveform drawing button 1201 of the second setting process screen in FIG. 12, the separated waveform drawing screen of this example is displayed. The separated waveform drawing screen of this example has a separated waveform drawing button 1301, an apex coordinate edit button 1302, a define button 1303, a cancel button 1304, a separated waveform parameter display field 1305, a read button 1306, a save button 1307, a cancel button 1308 and a graph region 1309. A sample waveform for which a separating method is to be set is displayed on the graph region 1309 on an initial screen. The parameters set on the separated waveform parameter setting field 1204 of the second setting process screen in FIG. 12 are displayed on the separated waveform parameter display field 1305.

Indicators which show the retention time, the base line starting time, the base line end time and the sampling period displayed on the separated waveform parameter display field 1305 are displayed on the graph region 1309. When clicking the separated waveform drawing button 1301, the user can draw two waveforms included in the sample waveform. The user can easily draw the two waveforms using the indicators displayed on the graph region 1309. When clicking the apex coordinate edit button 1302, the user can edit the apex coordinate. The editing of the apex coordinate is described with reference to FIG. 6. When the user clicks the define button 1303, the drawn two separated waveforms are defined. When the user clicks the save button 1307, the separated waveform created by the second setting process is saved as the separating method in the peak shape library. When the user clicks the read button 1306, the separated waveform can be read as the separating method saved in the peak shape library.

FIG. 14 illustrates an example of the base line drawing screen displayed on the display device. When the user clicks the base line drawing button 1202 of the second setting process screen in FIG. 12, the base line drawing screen of this example is displayed. The base line drawing screen of this example has a base line drawing button 1401, a define button 1402, a cancel button 1403, a separated waveform parameter display field 1404, a read button 1405, a save button 1406, a cancel button 1407 and a graph region 1408.

The sample waveform displayed on the graph region 1208 of the second setting process screen in FIG. 12 is displayed on the graph region 1408. The parameters set on the separated waveform parameter setting field 1204 of the second setting process screen in FIG. 12 are displayed on the separated waveform parameter display field 1404.

When the user clicks the base line drawing button 1401, a field for specifying the separating method of the sample waveform is displayed. The user can select the separating method from the list including the vertical line division, the leading division, the tailing division and the like. The user can draw a base line for the sample waveform according to the selected separating method. For example, the base line is drawn by the vertical line method, the forward horizontal line method, the backward horizontal line method or the like. In the example of FIG. 14, the user selects the vertical line division as the separating method, and draws the base line according to the vertical line method.

When the user clicks the define button 1402, the drawn base line is defined. When the user clicks the save button 1406, the base line created by the second setting process is saved as the separating method into the peak shape library. When the user clicks the read button 1405, the base line can be read as the separating method created by the second setting process saved in the peak shape library.

Figure 15:
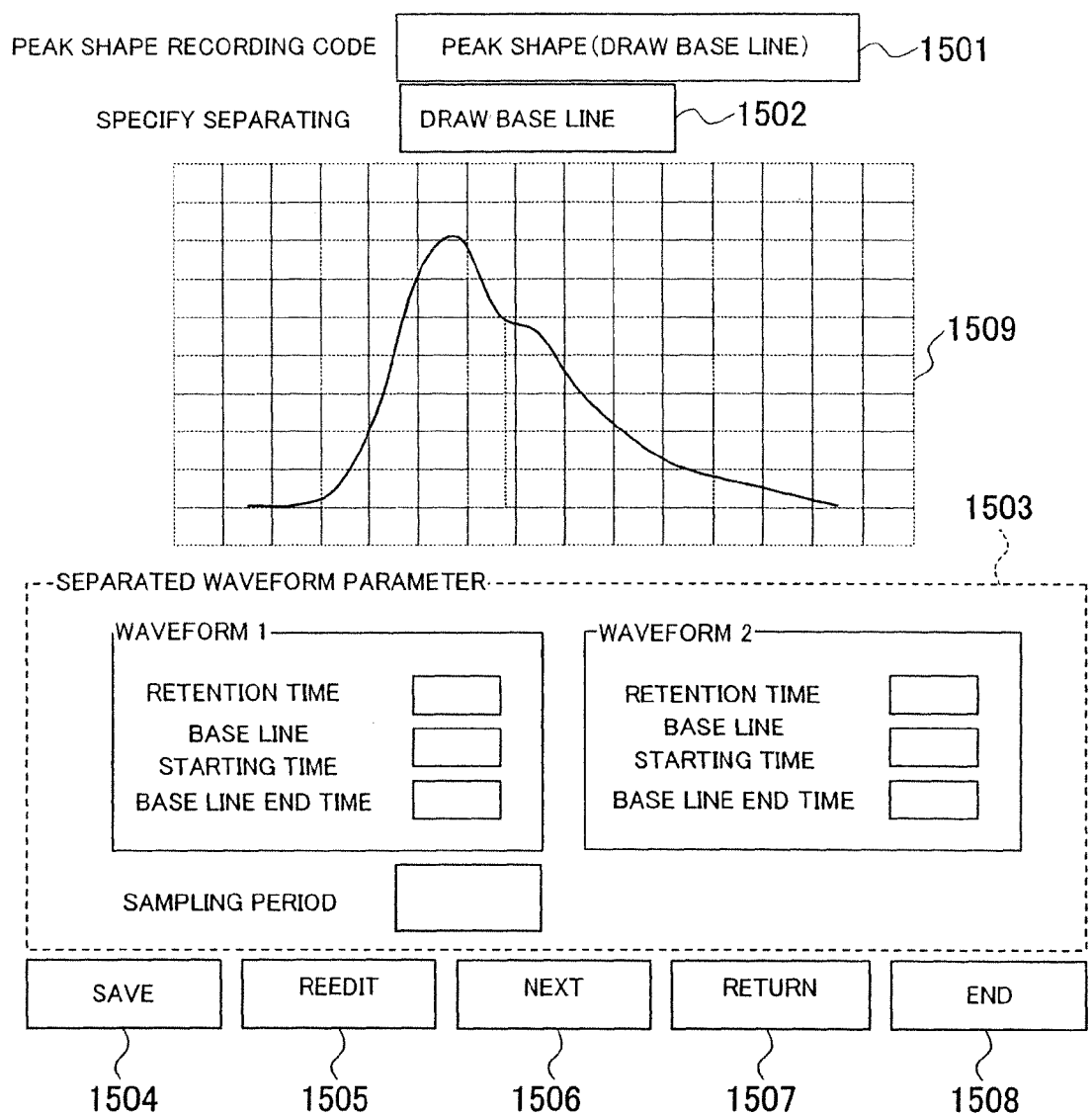
FIG. 15 is a diagram illustrating an example of a base line display screen by means of the viewer function displayed on the display device of the chromatograph analyzing device according to the present invention.

FIG. 15 illustrates a display state of the base line display screen displayed on the display device. The example of the base line saved in the peak shape library can be displayed by using the viewer function. The base line display screen of this example has a peak shape registration code field 1501, a separating method specifying field 1502, a separating waveform parameter display field 1503, a save button 1504, a reedit button 1505, a next button 1506, a return button 1507, an end button 1508, and a graph region 1509. The sample waveform is displayed on the graph region 1509.

In the example of FIG. 15, the base line drawing is displayed on the separating method specifying field 1502. The graph region 1509 shows that the sample waveform is separated by the vertical line division. This means that the user draws the base line according to the vertical line separating method so as to separate the sample waveform into two.

When the user clicks the reedit button 1505, the base line can be reedited. When the user clicks the save button 1504, the reedited result can be saved in the peak shape library. When the user clicks the next button 1506, a next base line saved in the peak shape library is displayed. When the user clicks the return button 1507, a previous base line saved in the peak shape library is displayed. When the user clicks the end button 1508, the base line display screen can be ended.

FIG. 16 illustrates an example of a time table information setting screen for the waveform process displayed on the display device. The waveform process time table information setting screen of this example has a waveform process time table 1601 and a peak shape library name specifying field 1602. The user sets a schedule of the base line drawing method on the waveform process time table 1601. At this time, the user sets a waveform processing interval to be subject to the base line setting process. The waveform process time table 1601 includes elapsed time, function, numerical value and on/off fields in this order from the left. The waveform process base line drawing method is specified for the function field.

In the example of FIG. 16, a base line N method is used. The forward horizontal line method is ON at elapsed time of 1.0 minute, and the forward horizontal line method is OFF at elapsed time of 3.0 minutes. The base line is drawn by the forward horizontal line method for 2 minutes from elapsed time of 1.0 minute to 3.0 minutes. The base line setting is ON at elapsed time of 3.5 minutes, and the base line setting is OFF at elapsed time of 4.5 minutes. The base line setting process is automatically executed on the chromatograph data for 1 minute from elapsed time of 3.5 minutes to 4.5 minutes. The backward horizontal line method is ON at elapsed time of 5.0 minutes, and the backward horizontal line method is OFF at elapsed time of 5.5 minutes. The base line is drawn by the backward horizontal line method for 0.5 minute from elapsed time of 5.0 minutes to 5.5 minutes.

According to the waveform process time table of this example, the waveform process base line drawing methods which are different from each other can be specified in a plurality of intervals.

The user can specify the separating method to be used for the base line setting on the peak shape library name specifying field 1602, by using the peak shape library.

Figure 17:
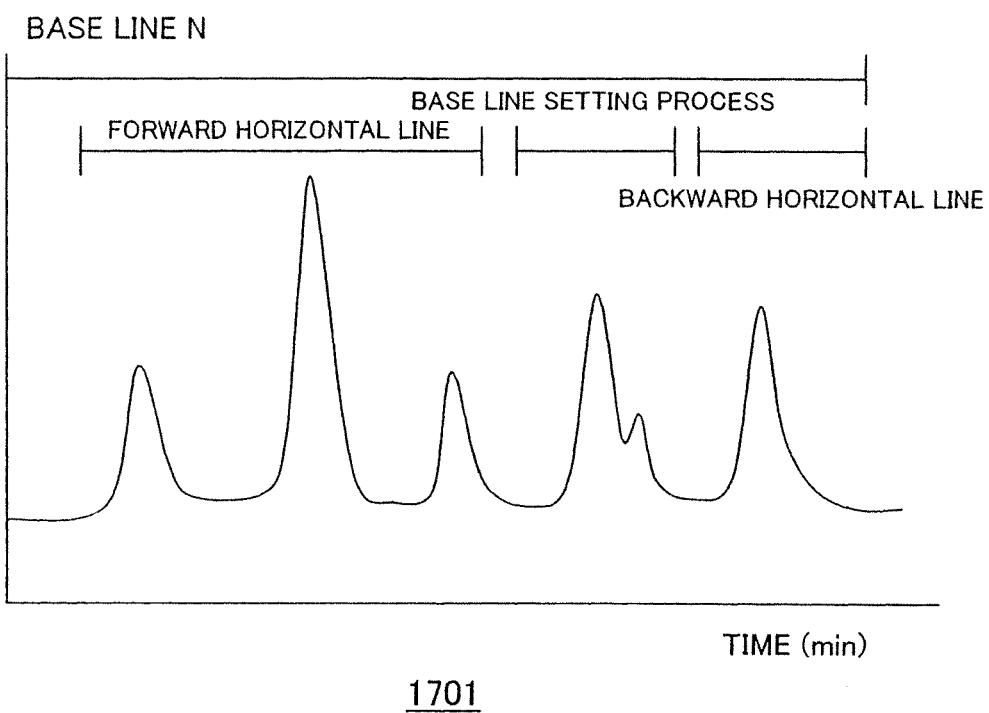
FIG. 17 is a diagram illustrating an example of a chromatograph data display screen displayed on the display device of the chromatograph analyzing device according to the present invention.

FIG. 17 illustrates an example of the chromatograph data display screen displayed on the display device. Effective range information of the waveform process time table is displayed for a waveform of the chromatograph data on the chromatograph data display screen of this example. An example of the waveform process time table 1601 in FIG. 16 is displayed.

According to this example, when the reanalyzing process is executed, while this display screen is being viewed, the waveform process time table can be set. That is to say, while the unseparated peak waveform included in the chromatograph data is being viewed, the base line setting process can be set in the waveform process time table.

When the waveform process is executed on the chromatograph data according to the base line setting conditions created by the user, a base line code which represents that the base line setting process has been applied, a peak shape library name and a peak shape registration code in the peak shape library are output onto the quantitative calculation result in the report. As a result, the user can easily check that the waveform process is executed according to the base line setting conditions.

The examples of present invention are explained, but a person skilled in the art can easily understand that the present invention is not limited to these and can be variously modified within a range of the present invention described in claims.

What is claimed is:

1. A chromatograph analyzing device comprising:
a chromatograph unit for separating a component included in a sample;
a data processing device for processing chromatograph data obtained from the chromatograph unit;
a display device for displaying the chromatograph data; and
a storage device for saving base line setting conditions as waveform processing conditions for an unseparated peak appearing in the chromatograph data,
wherein the base line setting conditions include a sample waveform which expresses a waveform of an unseparated peak expected to appear in the chromatograph data and a separation method using a base line specified by a user for the unseparated peak in the chromatograph data displayed on the display device, and
the data processing device, based on a comparison between a configuration of sample waveform saved in the storage device and a configuration of the unseparated peak in the chromatograph data, separates the unseparated peak using a base line specified by a user saved in the storage device by any of the separation methods selected by the user and saves a separated waveform prepared by the separation method in the storage device.

2. The chromatograph analyzing device according to claim 1, wherein the data processing device uses the separated waveform prepared by the separation method, which is saved in the storage device, as the separation condition.

3. The chromatograph analyzing device according to claim 1, wherein the separating method specified by the user includes a vertical line method, a forward horizontal line method, or a backward horizontal line method.

4. The chromatograph analyzing device according to claim 1, wherein the common parameters are set for the separating method specified by the user.

5. The chromatograph analyzing device according to claim 1, wherein the display device displays a setting process screen for setting a separating method to be specified by the user and the setting process screen has a separating method specifying field for specifying the separating method, a base line drawing method specifying field for specifying a base line drawing method, and a separated waveform parameter setting field for setting parameters common with the separating method.

* * * * *